(12) United States Patent
Sim et al.

(10) Patent No.: US 10,106,861 B2
(45) Date of Patent: Oct. 23, 2018

(54) MICROALGAE WITH IMPROVED PHOTOTAXIS AND PHOTOSYNTHETIC EFFICIENCY

(71) Applicant: Korea University Research and Business Foundation, Seoul (KR)

(72) Inventors: Sang Jun Sim, Seoul (KR); Ho-Seok Kwak, Seoul (KR); Young Hwan Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 15/424,866

(22) Filed: Feb. 5, 2017

(65) Prior Publication Data
US 2018/0100206 A1 Apr. 12, 2018

(30) Foreign Application Priority Data

Oct. 12, 2016 (KR) .................. 10-2016-0132021
Dec. 20, 2016 (KR) .................. 10-2016-0174591

(51) Int. Cl.
C12N 1/12 (2006.01)
C12P 7/64 (2006.01)
C12R 1/89 (2006.01)

(52) U.S. Cl.
CPC .................. *C12R 1/89* (2013.01); *C12N 1/12* (2013.01); *C12P 7/64* (2013.01)

(58) Field of Classification Search
None
See application file for complete search history.

(56) References Cited

FOREIGN PATENT DOCUMENTS

KR 10-1471270 B1 12/2014

OTHER PUBLICATIONS

Dent, R.M., et al., "Functional Genomics of Eukaryotic Photosynthesis Using Insertional Mutagenesis of Chlamydomonas reinhardtii", "Plant Physiology", Feb. 2005, pp. 545-556, vol. 137.
Kim, J., et al., "Microfluidic High-Throughput Selection of Microalgal Strains with Superior Photosynthetic Productivity Using Competitive Phototaxis", "Scientific Reports", Feb. 8, 2016, pp. 21155-21165, vol. 6.
Matsuo, T., et al., "A systematic forward genetic analysis identified components of the Chlamydomonas circadian system", "Genes & Development", Mar. 11, 2008, pp. 918-930, vol. 22.
Ochman, H., et al., "Genetic Applications of an Inverse Polymerase Chain Reaction", "Genetics", Nov. 1988, pp. 621-623, vol. 120.

*Primary Examiner* — Yong D Pak
(74) *Attorney, Agent, or Firm* — Hultquist, PLLC; Steven J. Hultquist (57) ABSTRACT

The present invention relates to microalgae with improved phototaxis and photosynthetic efficiency, and more particularly, to a microalgae PTS42 (KCTC18499P) mutant of *Chlamydomonas reinhardtii* and uses thereof. In the microalgae PTS42 according to the present invention of which photosensitivity and photosynthetic efficiency are improved due to excellent phototaxis, conversion of carbon dioxide into biomass is excellent as compared to a wild type strain and a maximum photosynthesis rate and lipid accumulation ability are also high, such that the microalgae PTS42 are useful as a photosynthetic strain for constructing a biofuel production process as well as an effect of decreasing carbon dioxide.

9 Claims, 11 Drawing Sheets
(10 of 11 Drawing Sheet(s) Filed in Color)
Specification includes a Sequence Listing.

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: UP3

<400> SEQUENCE: 1
gactcacctc ccagaattcc tgg                    23

<210> SEQ ID NO 2
<211> LENGTH: 22
<212> TYPE: DNA
<213> ORGANISM: Artificial Sequence
<220> FEATURE:
<223> OTHER INFORMATION: UP2

<400> SEQUENCE: 2
tcgttccgca ggctcgcgta gg                     22

<210> SEQ ID NO 3
<211> LENGTH: 30
<212> TYPE: DNA
<213> ORGANISM: Artificial Sequence
<220> FEATURE:
<223> OTHER INFORMATION: UP1

<400> SEQUENCE: 3
tcgagaagta acagggattc ttgtgtcatg             30

<210> SEQ ID NO 4
<211> LENGTH: 23
<212> TYPE: DNA
<213> ORGANISM: Artificial Sequence
<220> FEATURE:
<223> OTHER INFORMATION: DP4

<400> SEQUENCE: 4
cctcgaggtg ttcgaggaga ccc                    23

-continued

```
<210> SEQ ID NO 5
<211> LENGTH: 23
<212> TYPE: DNA
<213> ORGANISM: Artificial Sequence
<220> FEATURE:
<223> OTHER INFORMATION: DP3

<400> SEQUENCE: 5
cgctggatct ctccggcttc acc                                              23

<210> SEQ ID NO 6
<211> LENGTH: 20
<212> TYPE: DNA
<213> ORGANISM: Artificial Sequence
<220> FEATURE:
<223> OTHER INFORMATION: DN1

<400> SEQUENCE: 6
gaactggcgc agttcctctg                                                  20

<210> SEQ ID NO 7
<211> LENGTH: 14
<212> TYPE: DNA
<213> ORGANISM: Artificial Sequence
<220> FEATURE:
<223> OTHER INFORMATION: RMD227
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 7
ntcgwgwtsc nagc                                                        14

<210> SEQ ID NO 8
<211> LENGTH: 25
<212> TYPE: DNA
<213> ORGANISM: Artificial Sequence
<220> FEATURE:
<223> OTHER INFORMATION: 42R

<400> SEQUENCE: 8
ggacaccaag ayagcaagaa gaagc                                            25

<210> SEQ ID NO 9
<211> LENGTH: 20
<212> TYPE: DNA
<213> ORGANISM: Artificial Sequence
<220> FEATURE:
<223> OTHER INFORMATION: HgPrF

<400> SEQUENCE: 9
aggtcttccc ggaactgctg                                                  20

<210> SEQ ID NO 10
<211> LENGTH: 20
<212> TYPE: DNA
<213> ORGANISM: Artificial Sequence
<220> FEATURE:
<223> OTHER INFORMATION: HgPrR

<400> SEQUENCE: 10
agaggaactg cgccagttcc                                                  20
```

MICROALGAE WITH IMPROVED PHOTOTAXIS AND PHOTOSYNTHETIC EFFICIENCY

CROSS-REFERENCE TO RELATED APPLICATIONS

This application claims priority under 35 U.S.C. § 119 of Korean Patent Application No. 10-2016-0132021 filed Oct. 12, 2016 and Korean Patent Application No. 10-2016-0174591 filed Dec. 20, 2016. The disclosures of such Korean priority patent applications are hereby incorporated herein by reference in their respective entireties, for all purposes.

TECHNICAL FIELD

The present invention relates to microalgae with improved phototaxis and photosynthetic efficiency, and more particularly, to a microalgae PTS42 (KCTC18499P) mutant of *Chlamydomonas reinhardtii* and uses thereof.

BACKGROUND ART

As various environmental problems have occurred due to use of fossil fuel and an increase in carbon dioxide in the air, the development of an alternative energy source has been required. Solar energy is a continuous and infinite energy source, and since solar energy supplied to the earth for 1 hour may meet energy consumed in the world for a year, a method of converting solar energy into usable fuel may provide an ultimate solution for solving an energy depletion problem.

Microalgae, which are organisms capable of converting more than half of 120 TW supplied from the sun into a useful energy source such as biomass, lipid, or the like, through biosynthesis, has been spotlighted as a novel energy source. However, there is a limitation in converting infinite solar energy due to low photosynthetic efficiency of photosynthetic organisms itself. Theoretical maximum photosynthetic efficiency is 8 to 10% under continuous light conditions, but actually, it is difficult to achieve the maximum photosynthetic efficiency due to flexible light intensity and an inhibition action of strong light on photosynthesis. Therefore, at the time of mass cultivation of microalgae, cells existing on a surface of a reactor are subjected to a photo-oxidative damage by strong light, and photo-energy transferred to cells existing inside the reactor receives is small, such that the cells existing inside the reactor is subjected to photosynthesis inhibition, which decreases photo-energy conversion efficiency by at most 95%. Therefore, in order to improve productivity in a process of utilizing photosynthetic organisms, it is essential to adjust a balance between absorbing photo-energy and using the photo-energy.

As one of the methods of improving photosynthetic efficiency of the microalgae, a method of decreasing a chlorophyll antenna size has been used. 100 or more genes participate in and regulate photosynthesis mechanism, which is one of the most complicated biochemical mechanisms, and a large number of proteins and coenzymes are required for an electron transport system, carbon dioxide fixation, and synthesis of photosynthetic pigments. Therefore, the method of improving photosynthetic efficiency through a method of inhibiting chlorophyll b synthesis to decrease the antenna size is insufficient as an ultimate solution, such that a more efficient selection method is required.

The microalgae evolutionally have phototaxis to sense directionality with respect to light stimulation and move toward a desired position at the same time. In the case in which the microalgae do not have phototaxis, a photodamage or photosynthesis inhibition phenomenon may occur with respect to various light stimulations. Therefore, regulation of phototaxis in the microalgae may be considered as one of the main factors for optimal photosynthesis.

Therefore, the present inventors tried to select strains having a rapid cell growth property and excellent lipid productivity as compared to existing wild-type strains, and confirmed that in the case of selecting strains having excellent phototaxis with respect to light at a cellular level using phototaxis of microalgae, strains having improved photosynthetic efficiency and growth property may be easily and efficiently secured, thereby completing the present invention.

DISCLOSURE

An object of the present invention is to provide microalgae PTS42 (KCTC18499P) mutant of *Chlamydomonas reinhardtii* which improved phototaxis and photosynthetic efficiency, and a method of producing a lipid or biomass using the same.

According to an aspect of the present invention, there is provided a microalgae PTS42 (KCTC18499P) mutant of *Chlamydomonas reinhardtii* which improved phototaxis and photosynthetic efficiency.

According to another aspect of the present invention, there is provided a method for producing a lipid including culturing the microalgae as described above to produce lipid.

According to another aspect of the present invention, there is provided a method for producing biomass including culturing the microalgae as described above to produce biomass.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Unless otherwise defined herein, all of the technical and scientific terms used in the present specification have the same meanings as those understood by specialists skilled in the art to which the present invention pertains. Generally, nomenclature used in the present specification is well known and commonly used in the art.

According to the present invention, in order to secure economical efficiency of a biological carbon dioxide recycling process and prepare a steppingstone for commercialization by selecting microalgae with improved photosynthetic efficiency and growth property to provide microalgae having excellent lipid productivity in addition to a cell growth property, strains having excellent phototaxis with respect to light at a cellular level were secured using phototaxis of the microalgae. In the strains secured as described above, phototaxis was improved by about 1.8 times, a maximum photosynthesis rate was improved by 41% and 57% at low and high light intensities, respectively, and lipid accumulation ability was also increased by about 4 times, as compared to existing strains.

The present inventors designated a novel mutant strain described above as "*Chlamydomonas reinhardtii* PTS42" and deposited the mutant strain at Korean Collection for Type Cultures (KCTC) at the Korea Research Institute of Bioscience and Biotechnology under an accession number of KCTC18499P on Sep. 6, 2016.

Therefore, in one aspect, the present invention relates to a microalgae PTS42 (KCTC18499P) mutant of *Chlamydomonas reinhardtii* of which phototaxis and photosynthetic efficiency are improved.

As used herein, the term "microalgae", which is a common name of monads performing photosynthesis while having photosynthetic pigments, means aquatic organism with a micro-scale size, which grows by fixing carbon dioxide using light such as sun light, or the like, as an energy source and performing photosynthesis. The microalgae according to the present exemplary embodiment may include green algae, diatom, red algae, flagellates, prasinophytes, cryptophyceae, xanthophyceae, dinoflagellates, blue-green algae, or the like.

According to the present invention, the microalgae may be characterized in that lipid productivity is increased, and biomass productivity is increased.

In another aspect, the present invention relates to a method of preparing lipid including culturing a microalgae PTS42 (KCTC18499P) mutant of *Chlamydomonas reinhardtii* to produce lipid.

In another aspect, the present invention relates to a method of preparing biomass including culturing a microalgae PTS42 (KCTC18499P) mutant of *Chlamydomonas reinhardtii* to produce biomass.

According to the present invention, it is preferable that the culturing is performed at a light intensity of 300 to 750 µmol photons $m^{-2}$ $s^{-1}$, but is not limited thereto. Further, it is preferable that the culturing is performed at 23° C. under 5% $CO_2$ atmosphere, but is not limited thereto.

As used herein, the term "lipid", which is a material that is not dissolved in water but is well-dissolved in an organic solvent among materials configuring the microalgae, may be divided into simple lipid and complex lipid depending on an ingredient or chemical structure thereof. Examples of lipid include neutral fat, glycerol phospholipids, glycerol glycolipid, carotenoid, steroid, and the like. Particularly, the lipid of the microalgae includes a lot of neutral fat and has a molecular structure similar to that of petroleum based oil, and a lipid content in the microalgae is 10 times that in bean and 7 to 8 times that in peanut.

As used herein, the term "biomass" means various algae and plant resources generated by photosynthesis, that is, branches, leaves, roots, fruits, and the like, of wood, grass, and crops.

According to the present invention, the biomass may be interpreted as *Chlorella sorokiniana* HS strain which is cultured in a medium containing a high concentration salt and in which a lipid content in cells is increased, a culture product containing the strain, a culture fraction thereof, or the like, and the biomass may be used as a raw material of bio-diesel.

EXAMPLES

The present invention will be described in detail by the Examples. These Examples are only to illustrate the present invention in more detail, and those skilled in the art will appreciate that these Examples are not to be construed as limiting a technical scope of the present invention.

Example 1

Method of Preparing and Selecting Microalgae Mutant Strain

A wild type strain of *Chlamydomonas reinhardtii* CC125 was obtained from U.S. *Chlamydomonas* Resource Center. A random mutant was prepared by insertional mutation of the wild type strain. A gene (1,700 kb) including a hygromycin (antibiotic)-resistance sequence was randomly inserted into the wild type strain cells by electroporation. Cultured cells were smeared on a TAP solid medium (table 1) containing hygromycin (concentration: 15 μg/μl), thereby securing microalgae mutant strains.

TABLE 1

Components of TAP-C medium
TAP-C Medium

| ingredient | content (in 1 L water) |
|---|---|
| TAP salts (in 1 L water) | 25 ml |
| NH$_4$Cl 15.0 g | |
| MgSO$_4$7H$_2$0 4.0 g | |
| CaCl$_2$2H$_2$O 2.0 g | |
| Phosphate solution (in 100 ml water) | 0.375 ml |
| K$_2$HPO$_4$ 28.8 g | |
| KH$_2$PO$_4$ 14.4 g | |
| Hutner's trace elements | 1.0 ml |
| EDTA disodium salt 50 g (250 ml water) | |
| ZnSO$_4$7H$_2$O 22 g (100 ml water) | |
| H$_3$BO$_3$ 11.4 g (200 ml water) | |
| MnCl$_2$4H$_2$O 5.06 g (50 ml water)) | |
| CoCl$_2$6H$_2$O 1.61 g (50 ml water) | |
| CuSO$_4$5H$_2$O 1.57 g (50 ml water) | |
| (NH$_4$)$_6$Mo$_7$O$_{24}$4H$_2$O 1.10 g (50 ml water) | |
| FeSO$_4$7H$_2$0 4.99 g (50 ml water) | |
| Tris base | 2.42 g |
| HCl | 1.0 ml |

After about 10,000 mutant strains prepared as described above were transferred to a sterilized vessel at an exponential growth phase and mixed, the mixed strains were put into a micro device for selecting the strains based on phototaxis, and only strains having excellent response to light were selected and separated through light stimulation (Korean Patent Laid-Open Publication No. 10-2014-0094143). Thereafter, growth properties of the selected mutant strains were compared and analyzed, such that a strain having the most excellent growth property was finally selected.

Figure 1:
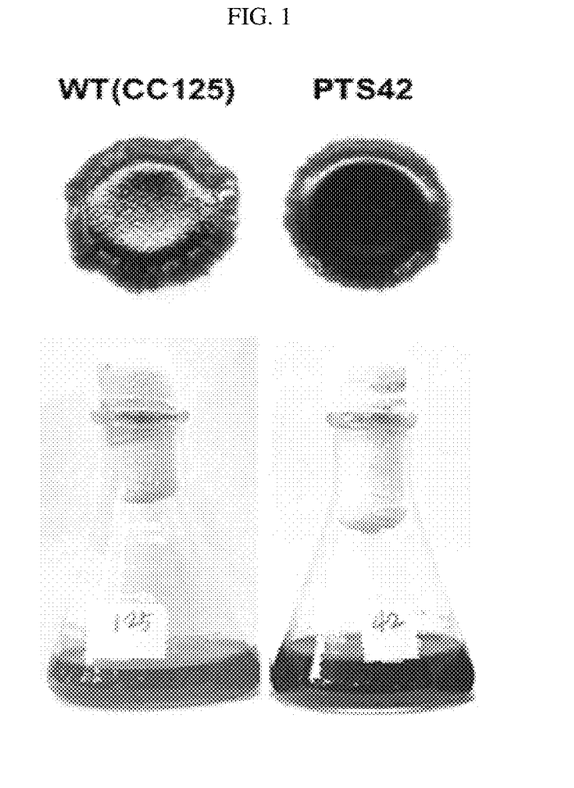
FIG. 1 illustrates images of a wild type *Chlamydomonas reinhardtii* strain CC125 and a PTS42 mutant strain of *Chlamydomonas reinhardtii* with improved phototaxis and photosynthetic efficiency in a solid medium and images thereof cultured in a flask.

As a result, a microalgae PTS 42 (KCTC18499P) mutant strain was selected (FIG. 1).

Example 2

Cell Size Analysis

Cell sizes of the wild type CC125 strain and the PTS42 mutant strain were compared through optical microscope images thereof.

Figure 2:
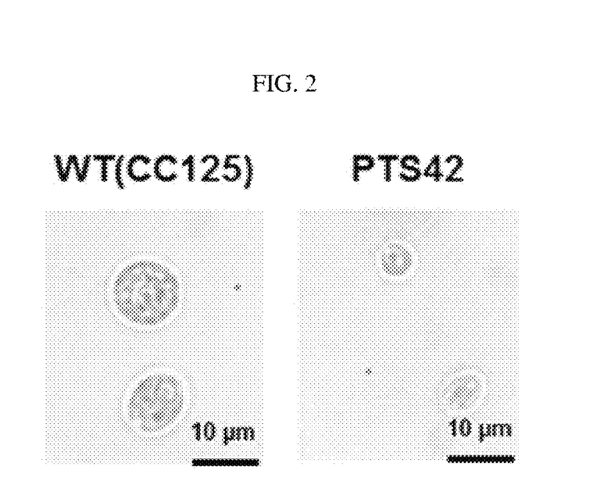
FIG. 2 illustrates optical microscope images of the wild type strain and the PTS42 mutant strain.

As a result, it may be appreciated that the cell size of the mutant strain was small as illustrated in FIG. 2.

Figure 3:
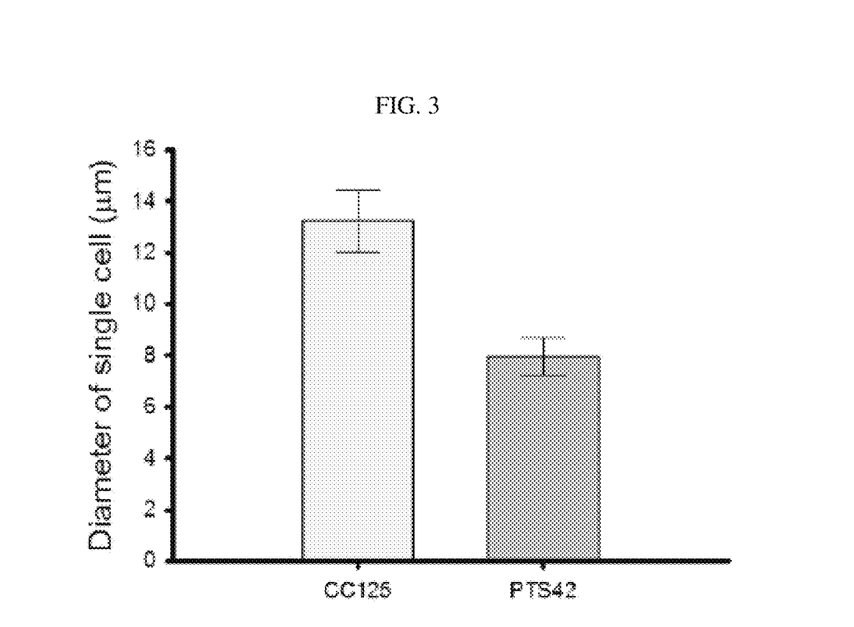
FIG. 3 is a graph illustrating average diameters of single cells of the wild type strain and the PTS42 mutant strain.
Figure 4:
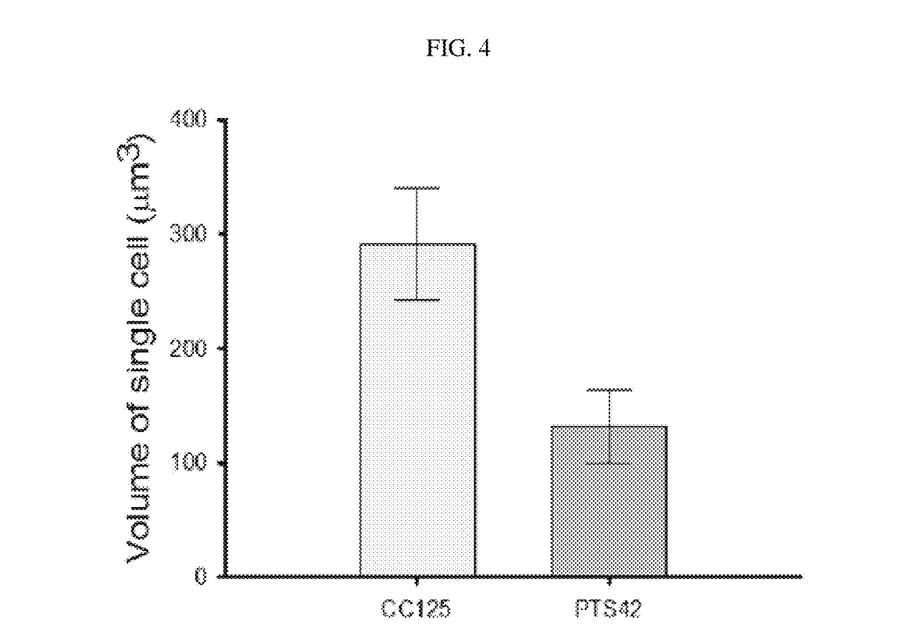
FIG. 4 is a graph illustrating average volumes of single cells of the wild type strain and the PTS42 mutant strain.

The result was analyzed using an image analysis program Image J, and as a result, it may be appreciated that a diameter of the cell was decreased by about 40 to 45%, and a volume thereof was decreased by about 50 to 55% (FIGS. 3 and 4).

Example 3

Phototaxis Analysis

In order to analyze phototaxis of the wild type strain and the PTS42 mutant strain with respect to light stimulation at a cellular level, phototaxis thereof was measured using a microfluidic system disclosed in Korean Patent Laid-Open Publication No. 10-2014-0094143.

Figure 5:
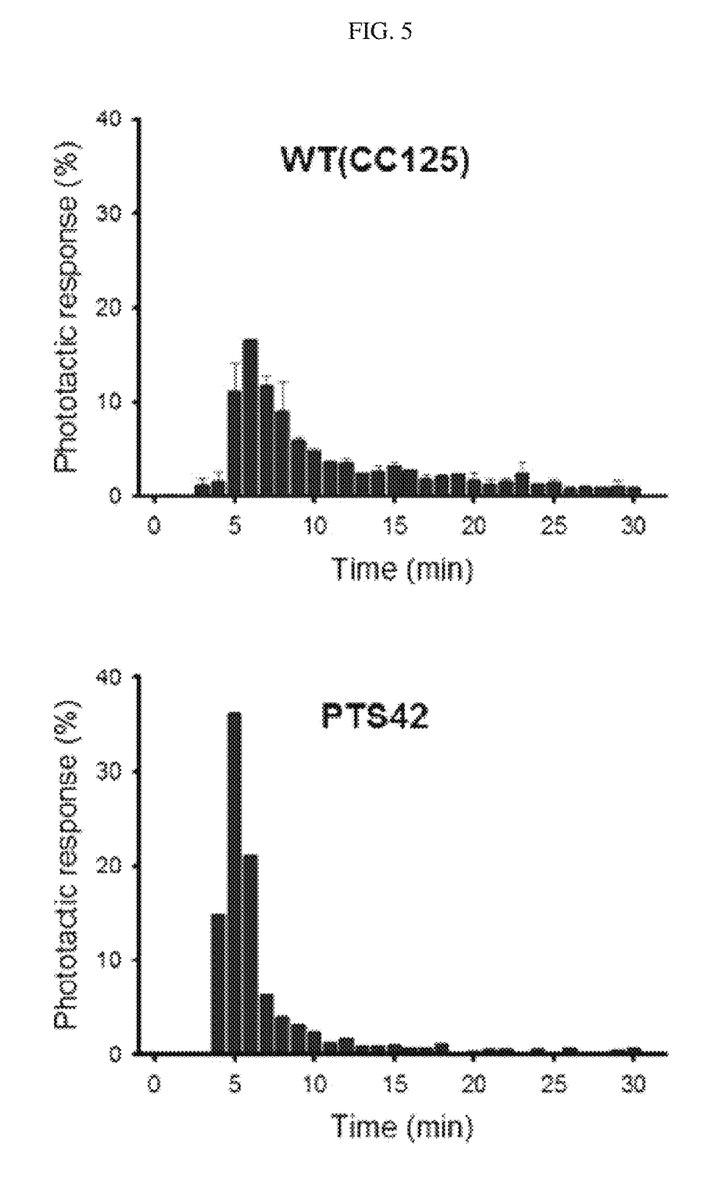
FIG. 5 is a histogram illustrating the number of cells exhibiting a phototactic response per minute in the wild type strain and the PTS42 mutant strain.

As a result of measuring the number of cells (per minute) moving a predetermined distance (3 cm) for 30 minutes with respect to light stimulation at a light intensity of 70 μmol photons m$^{-2}$ s$^{-1}$, it may be appreciated that in the case of the PTS42 mutant strain, most of the cells arrived within 3 to 5 minutes after light irradiation (FIG. 5). This shows that on average, response of the PTS42 mutant strain to light was rapid as compared to the wild type strain.

This result was statistically analyzed, thereby calculating an inverse of an average time required for the strain to arrive at a predetermined distance (3 cm) by light. That is, this graph shows that the higher the inverse value, on average, the faster the speed of the strain responding to light to move.

Figure 6:
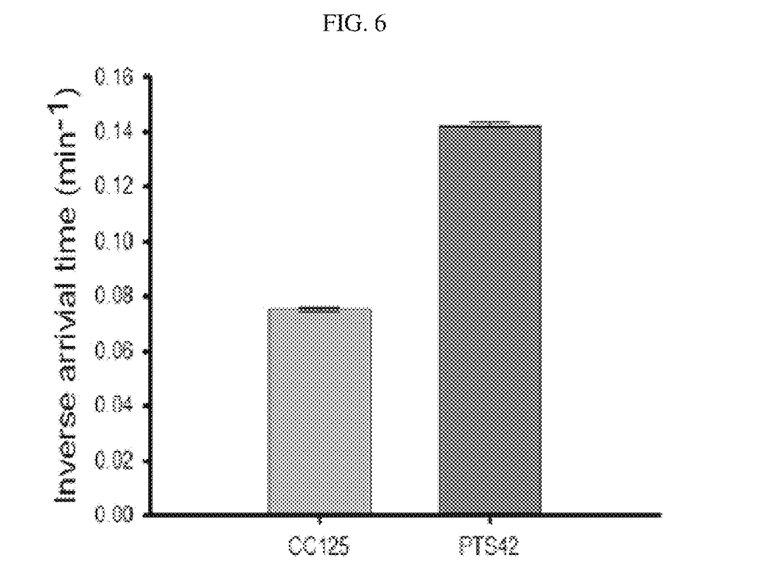
FIG. 6 is a graph illustrating an inverse of an average time required to move a predetermined distance depending on phototaxis of the wild type strain and the PTS42 mutant strain.

As a result, it may be appreciated that the speed of the PTS42 mutant strain responding to the light to move was improved by about 1.89 times as compared to the wild type strain as illustrated in FIG. 6.

Next, statistical skewness of a histogram for the number of cells arrived at the predetermined distance per minute was illustrated. This shows that the larger the skewness value, the faster the response to light and speed.

Figure 7:
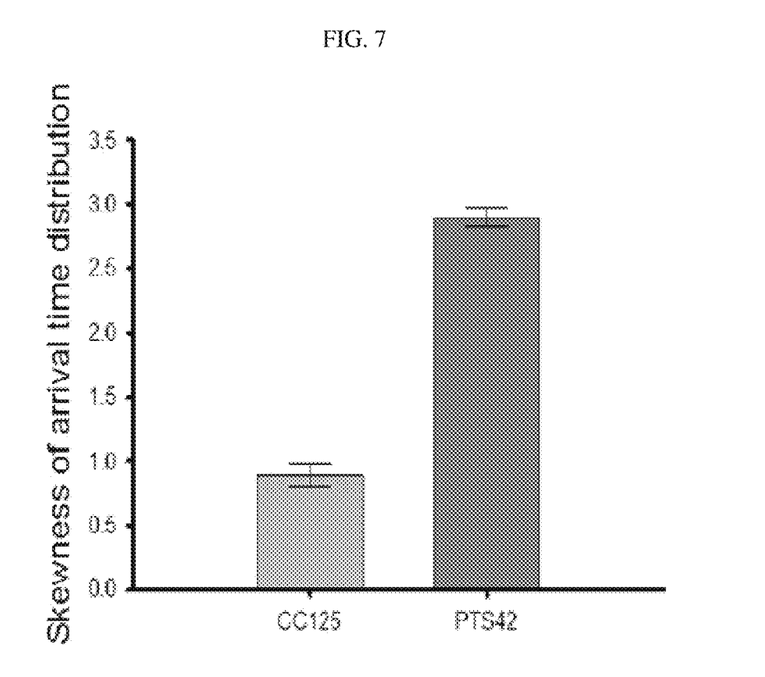
FIG. 7 is a graph illustrating skewness of a histogram for an average of the number of arrived cells depending on phototaxis of the wild type strain and the PTS42 mutant strain.

As a result, it was confirmed that in the PTS42 mutant strain, photosensitivity and photoresponse to light were significantly improved as compared to the wild type strain (FIG. 7).

Example 4

Photosynthetic Efficiency Analysis

Photosystem (PS)II operating efficiency, which is one of the indicators for measuring photosynthetic efficiency, of the wild type strain and the PTS42 mutant strain was analyzed. To this end, an amount of chlorophyll a in cells was measured, and the same standard amount of cells corresponding to 30 μg was transferred to a glass microfiber filter and measured using Fluorescence Monitoring System II equipment.

Figure 8:
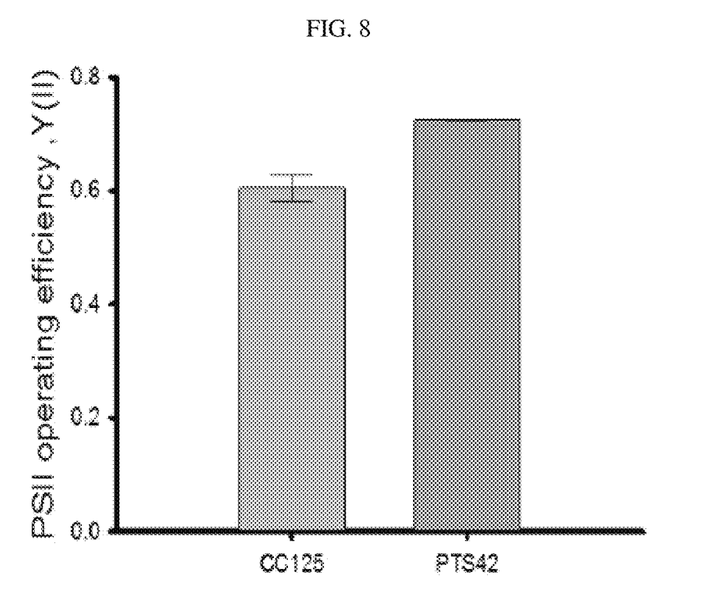
FIG. 8 is a graph illustrating photosystem (PS)II operating efficiency, which is one of the indicators illustrating photosynthetic efficiency, of the wild type strain and the PTS42 mutant strain.

As a result, it may be confirmed that in the PTS42 mutant strain, the photosystem (PS)II operating efficiency was improved by about 20% as compared to the wild type strain (FIG. 8).

Figure 9:
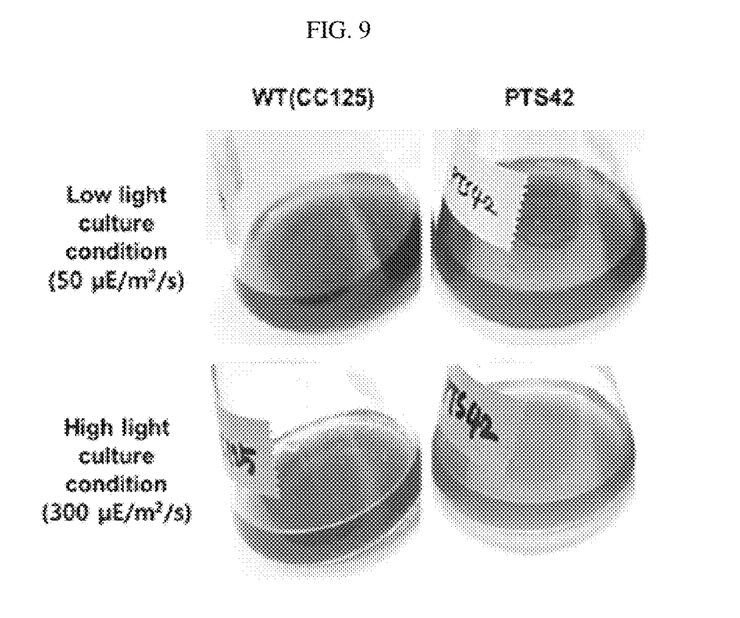
FIG. 9 illustrates images of the wild type strain and the PTS42 mutant strain cultured in a flask under low and high light conditions.

Next, the wild type strain and the PTS42 mutant strain were cultured in flasks, respectively, at low light intensity of 50 μmol photons m$^{-2}$ s$^{-1}$ and a high light intensity of 300 μmol photons m$^{-2}$ s$^{-1}$ (FIG. 9), and maximum rates of oxygen evolution and apparent quantum yields thereof were measured and analyzed under two conditions described above. The maximum rate of oxygen evolution, which is to measure and analyze oxygen generated by photosynthesis, is one of the indicators indicating photosynthetic efficiency, and the apparent quantum yield also is an indicator associated with photosynthetic efficiency.

Figure 10:
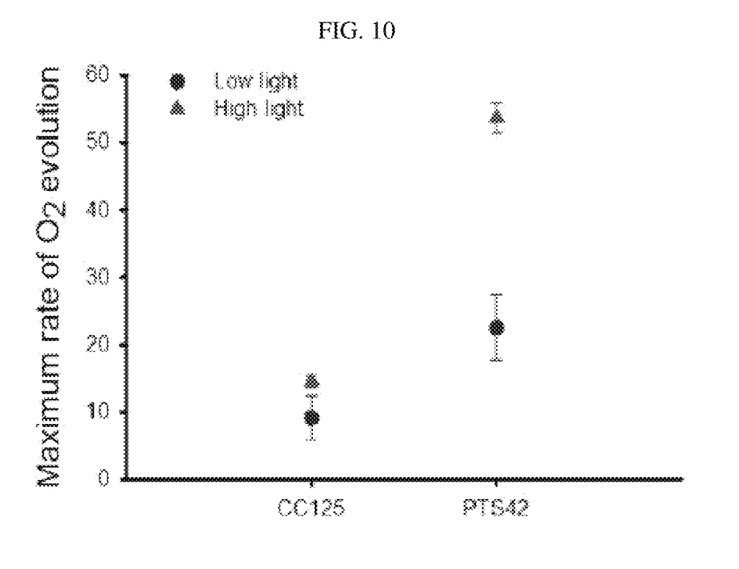
FIG. 10 is a graph illustrating a maximum rate of oxygen evolution, which is one of the indicators illustrating photosynthetic efficiency, of the wild type strain and the PTS42 mutant strain.
Figure 11:
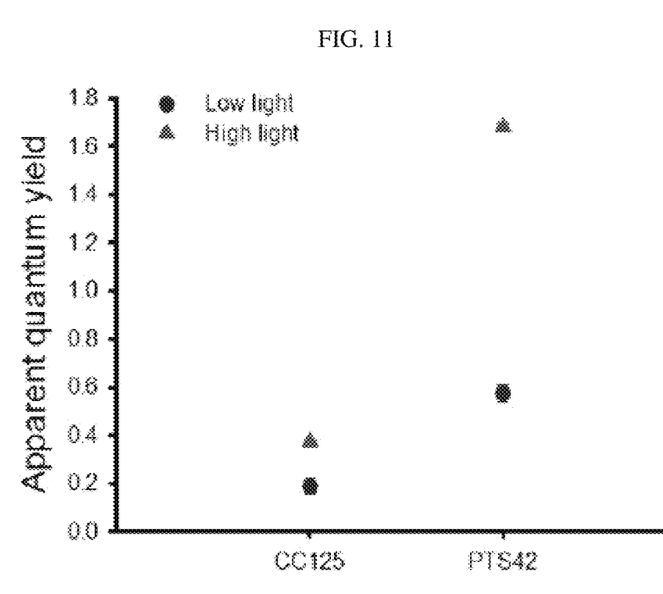
FIG. 11 is a graph illustrating an apparent quantum yield, which is one of the indicators illustrating photosynthetic efficiency, of the wild type strain and the PTS42 mutant strain.

As a result, it may be appreciated that in the PTS42 mutant strain, the maximum rate of oxygen evolution was improved under both conditions of the low and high light intensities as compared to the wild type strain, and when the light intensity was increased, a difference in oxygen amount generated by photosynthesis was increased (FIG. 10). That is, in the PTS42 mutant strain, as the light intensity was increased up to a predetermined level, photosynthetic efficiency was further increased. Further, in the apparent quantum yield analysis, it was confirmed that in the PTS42 mutant strain, the apparent quantum yield was high under both conditions of the low and high light intensities as compared to the wild type strain, equally to the maximum rate of oxygen evolution. Particularly, it was confirmed that as the light intensity was increased, an increase in the apparent quantum yield was increased as compared to the wild type strain, such that photosynthetic efficiency was significantly increased (FIG. 11).

Finally, a non-photochemical quenching (NPQ) value indicating energy that is not used in photosynthesis but dissipates among light energy inputted for photosynthesis was measured. The smaller the NPQ value, the higher the photosynthetic efficiency.

Figure 12:
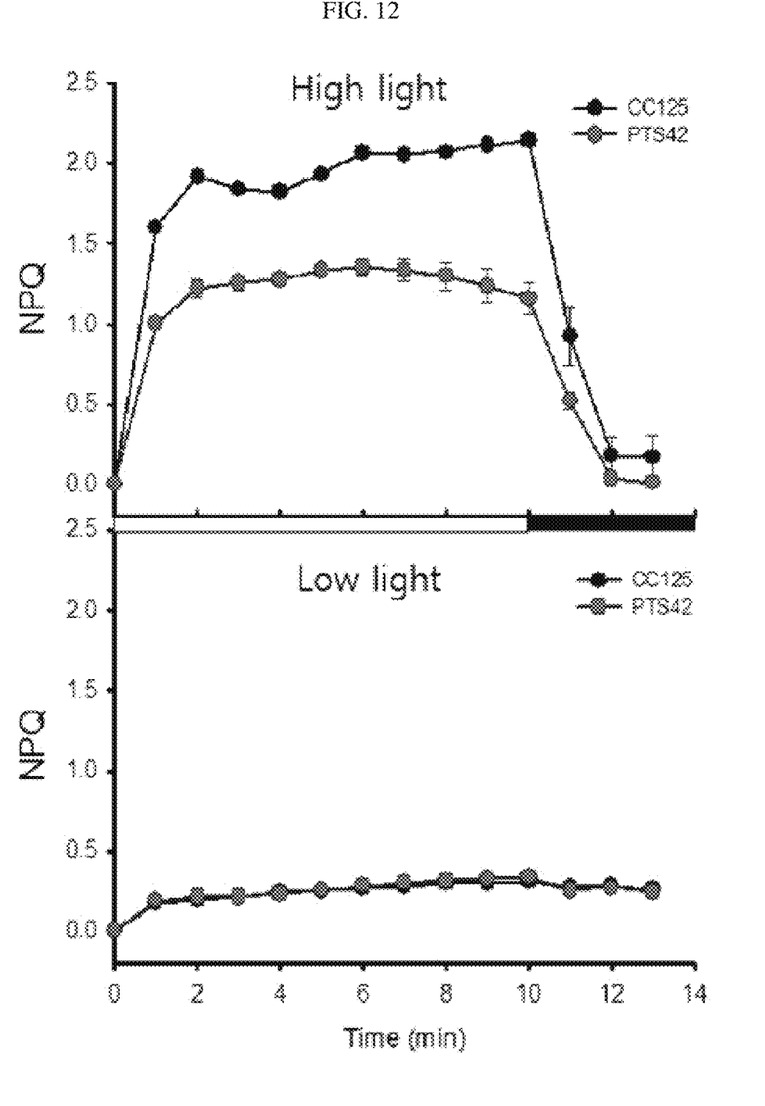
FIG. 12 is a graph illustrating non-photochemical quenching (NPQ), which is one of the indicators illustrating photosynthetic efficiency, of the wild type strain and the PTS42 mutant strain.

As a result, it may be appreciated that there was almost no difference in NPQ value between the wild type strain and the PTS42 mutant strain at a low light intensity of 50 μmol photons m$^{-2}$ s$^{-1}$, but when the light intensity was increased, in the PTS42 mutant strain, photosynthetic efficiency was improved (FIG. 12).

Example 5

Growth Property and Lipid Productivity Analysis in Photobioreactor

Figure 13:
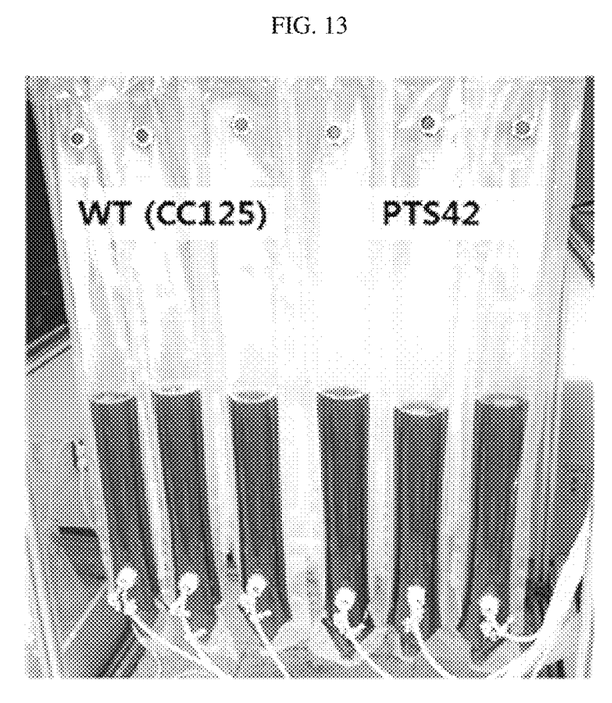
FIG. 13 illustrates images of the wild type strain and the PTS42 mutant strain cultured in a 5L-scale photobioreactor.
Figure 14:
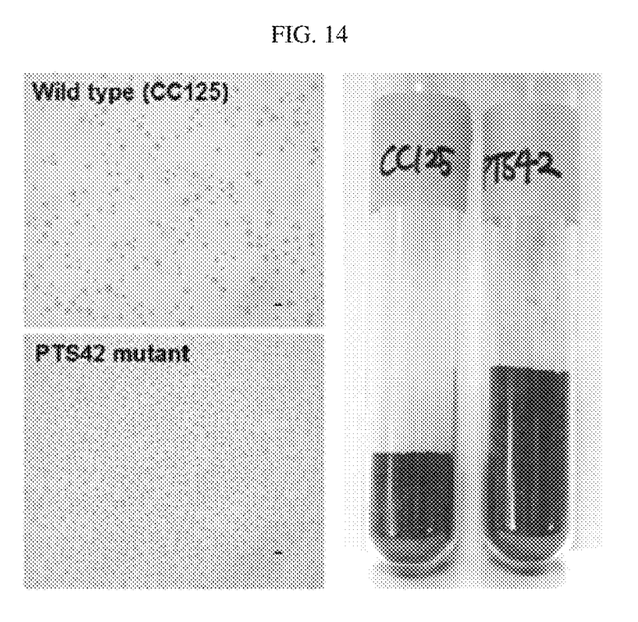
FIG. 14 illustrates optical microscope images of the wild type strain and the PTS42 mutant strain in the 5L-scale photobioreactor and production amounts of recovered biomass.

The wild type strain and the PTS42 mutant strain were cultured in a 5L-scale photobioreactor at a light intensity of 300 μmol photons m$^{-2}$ s$^{-1}$ under 5% $CO_2$ atmosphere for 3 days (FIG. 13), cell growth properties of the wild type strain and the PTS42 mutant strain were compared and analyzed.

Figure 15:
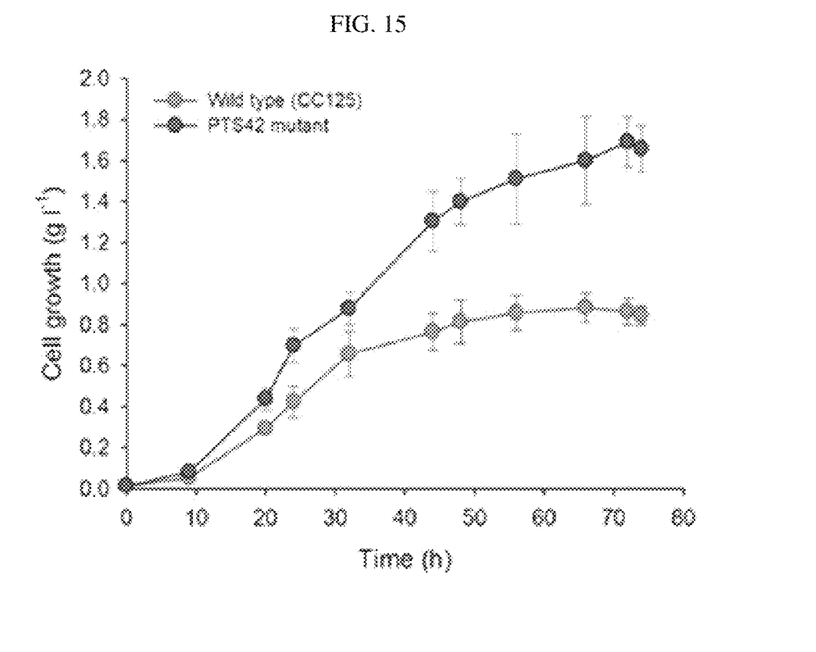
FIG. 15 is a graph illustrating cell growth of the wild type strain and the PTS42 mutant strain in the 5L-scale photobioreactor.

As a result, it may be confirmed that a maximum biomass production amount of the PTS42 mutant strain was about 1.7 g/L, and thus, biomass productivity was improved by about 1.8 times or more as compared to the wild type strain (FIG. 15).

Further, since it was confirmed in Example 4 that in the case of the PTS42 mutant strain, as the light intensity was increased, photosynthetic efficiency was improved, biomass productivity in the 5L-scale photobioreactor was compared and analyzed while increasing the light intensity.

Figure 16:
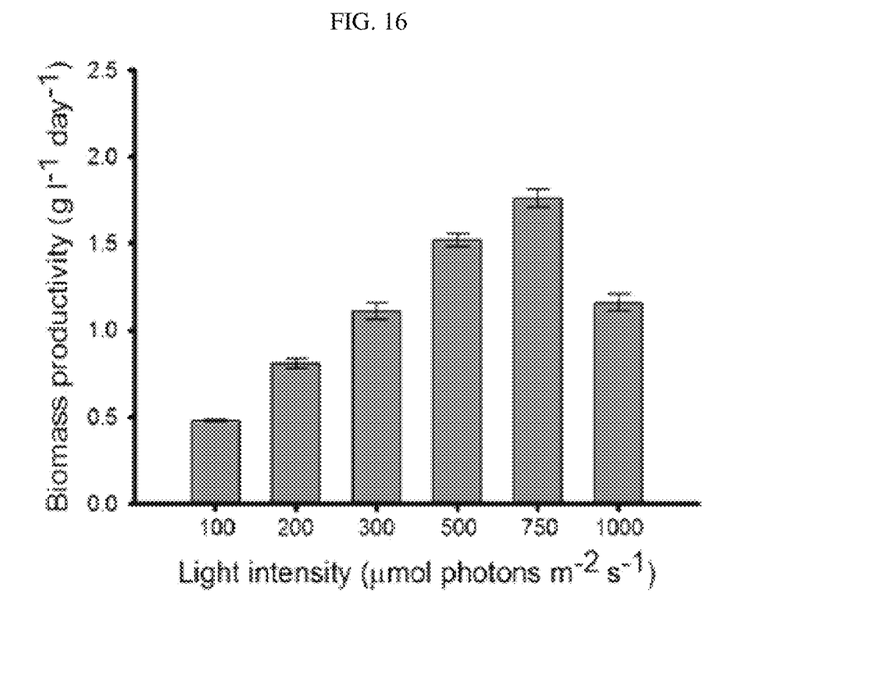
FIG. 16 is a graph illustrating biomass productivity of the PTS42 mutant strain in the 5L-scale bioreactor depending on light intensity.

As a result, it was confirmed that in the case of the PTS42 mutant strain, biomass productivity was increased to 1.74 g/L/d until the light intensity was increased to 750 μmol photons m$^{-2}$ s$^{-1}$, but biomass productivity was deteriorated at a light intensity higher than 750 μmol photons m$^{-2}$ s$^{-1}$ (FIG. 16).

Figure 17:
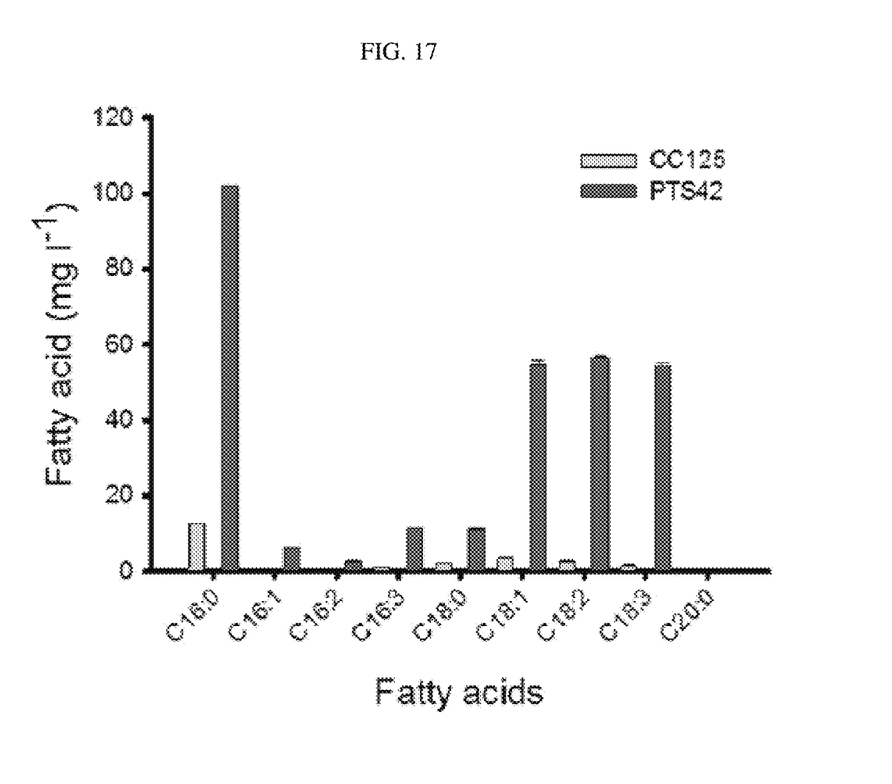
FIG. 17 is a graph illustrating lipid productivity of the wild type strain and the PTS42 mutant strain.

As a result of comparing lipid productivity of the wild type strain and the PTS42 mutant strain, it was confirmed that in the PTS42 mutant strain, lipid productivity was improved by about 8 times or more as compared to the wild type strain based on total fatty acids (FIG. 17). This result shows that in addition to photosynthetic efficiency associated with carbon dioxide conversion, lipid productivity was also improved, such that an economical microalgae process may be constructed.

Example 6

Insertion Position Analysis of PTS42 Mutant Strain in Genomic DNA

In order to analyze a position of a gene inserted into the mutant strain, PCR analysis was performed using primers capable of complementarily binding to flanking sequences on both sides of the inserted gene. Each of the used primers is illustrated in [Table 2].

TABLE 2

| SEQ ID | name | sequence (5'→3') | use |
|---|---|---|---|
| 1 | UP3 | GACTCACCTCCCAGAATTCCTGG | Specific primer for upstream sequence (primary) |
| 2 | UP2 | TCGTTCCGCAGGCTCGCGTAGG | Specific primer for upstream sequence (Secondary) |
| 3 | UP1 | TCGAGAAGTAACAGGGATTCTTGTGTCATG | Specific primer for upstream sequence (Tertiary) |
| 4 | DP4 | CCTCGAGGTGTTCGAGGAGACCC | Specific primer for downstream sequence (primary) |
| 5 | DP3 | CGCTGGATCTCTCCGGCTTCACC | Specific primer for downstream sequence (Secondary) |
| 6 | DN1 | GAACTGGCGCAGTTCCTCTG | Specific primer for downstream sequence (Tertiary) |
| 7 | RMD227 | NTCGWGWTSCNAGC | Degenerate primer |
| 8 | 42R | GGACACCAAGAYAGCAAGAAGAAGC | Sequence specific primer for mutant PTS42 |

Sequence analysis using PCR was performed using TAIL-PCR and PCR-SP methods known in the art (Dent R. M. et al., Plant Physiol. 137:545-556, 2005; Matsuo T. et al., Genes Dev. 22:918-930, 2008; Ochman H. et al., Genetics 120:621-623,1988).

Further, for southern blotting analysis, genomic DNA (10 μm) was cultured with 1 ml of Pst1 enzyme at 37° C., such that DNA was cleaved into several strands. The cleaved DNA was adsorbed in a positively charged nylon membrane (Zeta probe), and a probe capable of complementarily binding to the inserted gene was added thereto to thereby be bound thereto. The probe was prepared using the following primers (SEQ ID Nos. 9 and 10), and was labeled so that it is possible to identify the inserted gene through the adsorbed probe.

SEQ ID No. 9:
5'-AGGTCTTCCCGGAACTGCTG-3' (HgPrF)

SEQ ID No. 10:
5'-AGAGGAACTGCGCCAGTTCC-3' (HgPrR)

Figure 18:
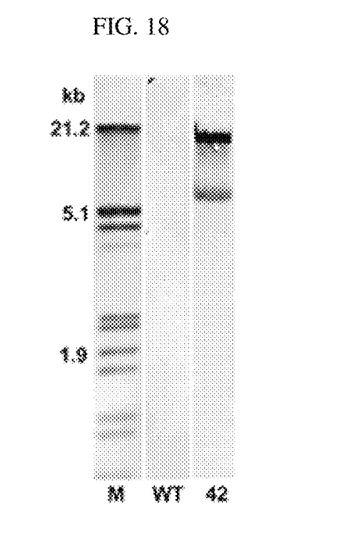
FIG. 18 illustrates southern blotting results of the wild type strain and the PTS42 mutant strain with respect to an inserted hygromycin-resistance gene.
Figure 19:
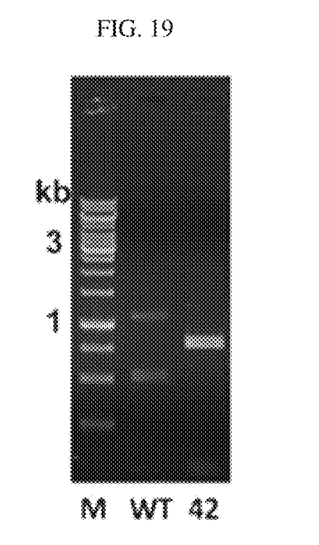
FIG. 19 is a result obtained by confirming an insertion position of the hygromycin-resistance gene in genomic DNA of the PTS42 mutant strain using polymerase chain reaction (PCR).

As a result, it may be appreciated that in the case of the PTS42 mutant strain, a hygromycin resistance gene inserted by random insertion was inserted into two sites of the genomic DNA (FIG. 18). A position of the gene in one of the two sites was identified, and the position was confirmed through PCR (FIG. 19). It may be appreciated that the hygromycin resistance gene was inserted at the position of the gene of PTS42 regulating synthesis of zinc finger protein as shown in [Table 3].

TABLE 3

| Mutant | Location | Protein ID | Function | Methods for sequence determination |
|---|---|---|---|---|
| PTS42 | Promoter (B) | 516641 | Protein binding; PHD-type zinc finger | TAIL-PCR & PCR-SP |

B: Both flanking sequences were identified
Protein ID was obtained from JGI Chlamydomonas v4.0
Function was described based on the JGI Chlamydomonas v4.0

In the microalgae PTS42 according to the present invention of which photosensitivity and photosynthetic efficiency are improved due to excellent phototaxis, conversion of carbon dioxide into biomass is excellent as compared to a wild type strain and a maximum photosynthesis rate and lipid accumulation ability are also high, such that the microalgae PTS42 are useful as a photosynthetic strain for constructing a biofuel production process as well as an effect of decreasing carbon dioxide.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof. A simple modification or change of the present invention may be easily performed by those skilled in the art, but this modification or change should be considered to be within the scope of the invention.

Deposit of Microorganisms
Depositary Name: Korea Research Institute of Bioscience and Biotechnology
Accession Number: KCTC18499P
Deposit Date: Sep. 6, 2016

The invention claimed is:

1. A microalgae PTS42 (KCTC18499P) mutant of *Chlamydomonas reinhardtii* which improved phototaxis and photosynthetic efficiency.

2. The microalgae of claim 1, wherein the microalgae have increased lipid productivity.

3. The microalgae of claim 1, wherein the microalgae have increased biomass productivity.

4. A method for producing a lipid, the method comprises culturing the microalgae PTS42 (KCTC18499P) mutant of *Chlamydomonas reinhardtii* of claim 1, and then producing said lipid.

5. The method of claim 4, wherein the culturing is performed at a light intensity of 300 to 750 μmol photons $m^{-2} s^{-1}$.

6. The method of claim 4, wherein the culturing is performed at 23° C. under 5% $CO_2$ atmosphere.

7. A method for producing biomass, the method comprises culturing the microalgae PTS42 (KCTC18499P) mutant of *Chlamydomonas reinhardtii* of claim 1.

8. The method of claim 4, wherein the culturing is performed at a light intensity of 300 to 750 μmol photons $m^{-2} s^{-1}$.

9. The method of claim 4, wherein the culturing is performed at 23° C. under 5% $CO_2$ atmosphere.

* * * * *